United States Patent

Chiba

[11] Patent Number: 5,133,133
[45] Date of Patent: Jul. 28, 1992

[54] HOLDER FOR CLAMPING USED MICROTOME BLADE

[75] Inventor: Tutomu Chiba, Souka, Japan

[73] Assignee: Kabushiki Kaisha Chiba Medikaru, Souka, Japan

[21] Appl. No.: 806,268

[22] Filed: Dec. 13, 1991

[30] Foreign Application Priority Data

Mar. 18, 1991 [JP] Japan ............... 3-23369[U]

[51] Int. Cl.⁵ ............................................. B26B 1/00
[52] U.S. Cl. ................................. 30/338; 30/329; 30/337
[58] Field of Search ............... 30/329, 338, 337, 342, 30/344

[56] References Cited

U.S. PATENT DOCUMENTS

| | | | |
|---|---|---|---|
| 917,102 | 4/1909 | Mossberg | 30/338 |
| 1,608,781 | 11/1926 | Efantis | 30/337 |
| 1,813,723 | 7/1931 | Beaver | 30/337 |
| 2,018,603 | 10/1935 | Case et al. | 30/337 |
| 2,203,714 | 6/1940 | Baer | 30/338 |
| 4,823,457 | 4/1989 | Prochaska | 30/342 |

Primary Examiner—Frank T. Yost
Assistant Examiner—Hwei-Siu Payer
Attorney, Agent, or Firm—Oblon, Spivak, McClelland, Maier & Neustadt

[57] ABSTRACT

A holder for reusing a used microtome blade, in which the front end portion of a holder body is cut through along a plane extending through the longitudinal axis of the holder body so as to form bifurcated half parts defining a slit for receiving a used microtome blade. An inclined through-bore is formed in the front front end portion, extending in the same plane so as to terminate the slit, one of the corners of the inserted end part of the microtome blade bears against the innermost part of the wall surface of the inclined throughbore and is clamped between the bifurcated half parts by a clamping member.

9 Claims, 2 Drawing Sheets

HOLDER FOR CLAMPING USED MICROTOME BLADE

BACKGROUND OF THE INVENTION

1. Field of the Invention

The present invention relates to a holder for clamping used microtome blade, in more particular to a holder which enables to safely reuse a used microtome blade as a trimming cutter or as a stationary cutter for cutting paper or the like.

2. Description of the Related Art

A microtome is exclusively used for preparing sliced thin samples to be examined with an optical or an electron microscope for observing tissue of a human body, animal or the like for the purpose of examination, studies and researches or the like in the field of medical science, the zoology, the botany or the like.

These microtome blades have usually been discarded whenever its sharpness has slightly degraded, since no more proper tissue samples having a smooth surface required for above-mentioned microscopic examination can be obtained by such a used and degraded microtome blade.

However, microtome blades whose sharpness has somewhat degraded by tissue slicing as mentioned above still have a sharpness sufficient for reusing them as a trimming knife for medical use or as a stationary knife or the like. Accordingly, there has been a strong demand for reusing such a used microtome blades. However, since the length of these microtome blades are relatively long as compared with the width and thickness thereof and they have still a certain extent of sharpness so as to be harmful to human fingers, direct handling of them by naked human fingers is difficult and dangerous.

SUMMARY OF THE INVENTION

The present invention has been proposed in view of the above-mentioned problem inherent to the prior art, and accordingly, one object of the present invention is to provide a holder for holding used microtome blades, which is simple in structure, and can be fabricated at a low cost while it can be easily and safely handled by human fingers.

According to the present invention, a holder for used microtome blade, comprising a bar-like body having one end part serving as a grip portion and the other end part formed therein with a slit formed by cutting the other end part therethrough substantially along the longitudinal axis thereof so that the slit extends inward from the end face of the other end part of the bar-like body to a middle position thereof at which a longitudinally inclined bore is formed for terminating the slit, and a means for clamping a microtome blade which is inserted in the slit so that one of the corners of an inserted end part of the microtome blade bears against the longitudinally inclined wall surface of the inclined bore.

With this arrangement in which the microtome blade inserted in the slit in the bar-like body is suitably clamped and one of the corners of the inserted end part thereof bears against the inclined wall of the inclined bore, the microtome blade can be held surely and safely while it can be prevented from being incidentally rotated in its longitudinal plane.

BRIEF DESCRIPTION OF THE DRAWINGS

The foregoing and other objects, features and attendant advantages of the present invention will be appreciated as the same become better understood by means of the following description and accompanying drawings wherein.

DESCRIPTION OF PREFERRED EMBODIMENTS

Figure 1:
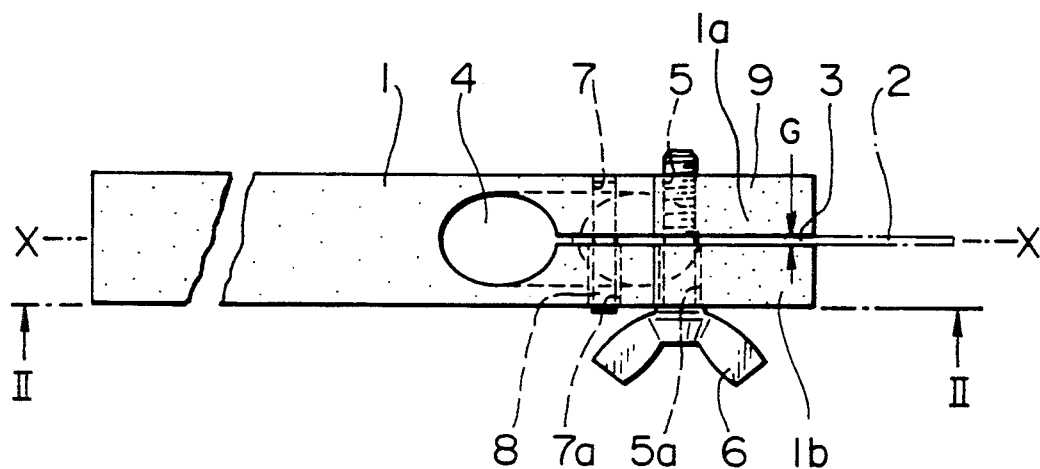
FIG. 1 is a top view illustrating a holder for clamping used microtome blades, in one embodiment form of the present invention.
Figure 2:
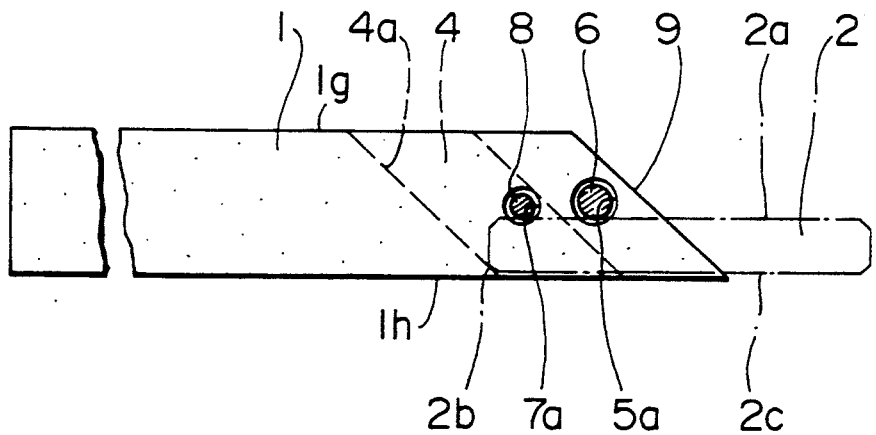
FIG. 2 is a sectional view along line II—II in FIG. 1.

Referring now to FIGS. 1 and 2 which show a holder for clamping used microtome blade, a plastic bar-like holder body 1 having a rectangular cross-sectional shape is cut in its front end portion so as to be formed therein a slit 3 in a plane substantially along the longitudinal axis X—X thereof. That is, the front end portion of the holder body 1 is bifurcated into two half parts 1a and 1b. The front face 9 of this front end portion is inclined, at which the front end of the slit 3 is opened to the outside. Further, the slit 3 extends through the front end portion, entirely in the heightwise direction. Further, a through-bore 4 is formed in the front end portion so as to slantly extend from the top face 1g to the bottom face 1h of the holder substantially in parallel with the inclined front end face 9 and in the plane in which the slit 3 is formed so that the slit 3 is terminated by this through-bore 4.

Figure 4:
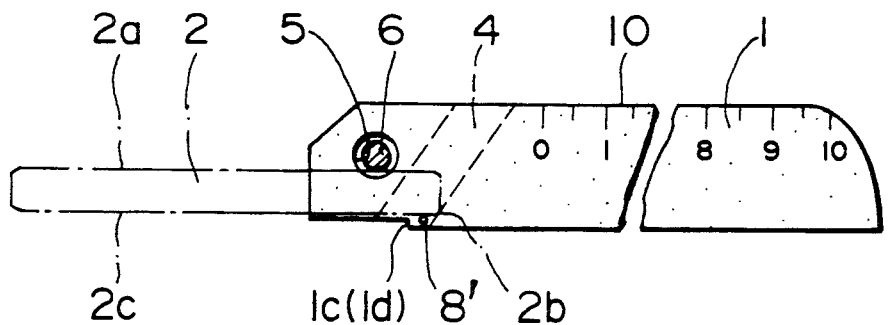
FIG. 4 is a sectional view along line IV—IV in FIG. 3.

It is to be noted that the through-bore 4 apparently has an elliptic shape from the top face 1g upto the bottom face 1h of the holder body 1 at which the through-bore 4 is opened to the outside, as shown in FIGS. 2 and 4, since the through-bore 4 is inclined with respect to the longitudinal axis X—X of the holder body 1.

A female thread hole 5 is formed in one half part 1a, extending crosswise thereof, and a blind hole 5a is formed in the other half part 1b, extending crosswise thereof and being aligned with the female thread hole 5. This hole 5a has a diameter slightly greater than that of the thread hole 5, and therefore, a thumbscrew 6 can be easily inserted through this hole 5a, and is then screwed into the female screw hole 5.

A blind pin hole 7 is formed in the one half part 1a, substantially in parallel with the through-hole 5a, and a hole 7a is formed in the other half part 1b, having a diameter slightly greater than the diameter of the blind pin hole 7 and being aligned with the same.

A blade hold pin 8, for preventing the microtome blade 2 from being turned around the shaft part of the thumbscrew 6 during use, is press-fitted in the blind pin hole 7 through the hole 7a. Although this blade hold pin 8 is necessary as a safe measure, it is not always essential in the arrangement of the present invention.

Since microtome blades 2 of all standardized types have common thickness of 0.254 mm, width of 8 mm, and the gap width G of the slit 3 is slightly larger than 0.254 mm. Further, the height and the width of the front end portion of the holder body 1 are preferably about 20 mm and 10 mm, respectively, and the inner diameter of the through bore 4 is set so as to allow both half parts 1a and 1b to resiliently deflect in order to clamp a microtome blade 2 inserted in the slit 3.

Next, explanation will be made hereinbelow on the use of the above-mentioned blade holder.

At first, the thumbscrew 6 is loosened so as to allow the half parts 1a and 1b to resiliently deflect slightly around the through-bore 4, and then a used microtome blade 2 is inserted into the slit 3 so that the cutting edge 2c thereof is extended along the bottom face of the holder body 1 while the top face 2a of the microtome blade 2 opposite to the cutting edge 2c bears against the blade hold pin 8 and the shank of the thumbscrew 6. Further, the microtome blade 2 is set in the thumbscrew 6. Further, the microtome blade 2 is set in the slit 3 so that the lower corner 2b of the inserted end part of the microtome blade 2 bears against the wall surface 4a of the inclined through-bore 4 at the inner-most part thereof. Then, the thumbscrew 6 is tightened to clamp the microtome blade 2 between the half parts 1a and 1b.

In this condition, the microtome blade 2 is projected from the front end face 9 of the holder body 1 by a substantial length sufficient for cutting paper or the like during use thereof. Since the top face 2a of the microtome blade 2 bears against the blade hold pin 8 and the thumbscrew 6 and since the lower corner 2b of the blade 2 bears against the innermost part of the wall surface 4a of the inclined through-bore 4, it is able to surely and safely hold the microtome blade 2 between the two halves 1a and 1b of the holder body 1 and to prevent the same from being turned even though a reaction force is exerted to the tip end part thereof during use.

Figure 3:
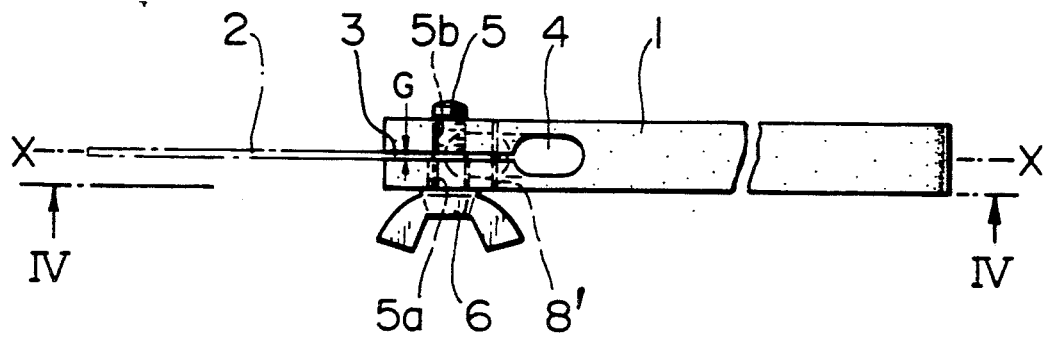
FIG. 3 is a top view illustrating a holder for clamping microtome blades in a second embodiment form of the present invention.

Referring to FIGS. 3 and 4, a second embodiment of the present invention will be explained. In these figures, like reference numerals are used to denote like parts to those shown in FIGS. 1 and 2 so that detailed explanation thereof is abbreviated for the sake of brevity.

In the second embodiment, the front end portion of the holder body 1 is cut out along the bottom surface of the holder so as to form a cut-out which extends upto a position intermediate of the through-bore 4, leaving bifurcated bottom side projecting parts 1c and 1d in the lower opening of the through-bore 4. The blade hold pin 8' is embedded near the end parts 1e and 1f of these bottom side projecting parts 1c and 1d and extending therebetween. Further, the grip portion of the holder body 1 is provided thereon with graduations 10 so that the grip end portion of the holder body 1 can be used as a measure.

The holder in the second embodiment can be used similar to the holder in the first embodiment, excepting that the bottom corner part 2b of the inserted part of the microtome blade 2 bears against the blade holder pin 8' in this second embodiment.

Figure 5:
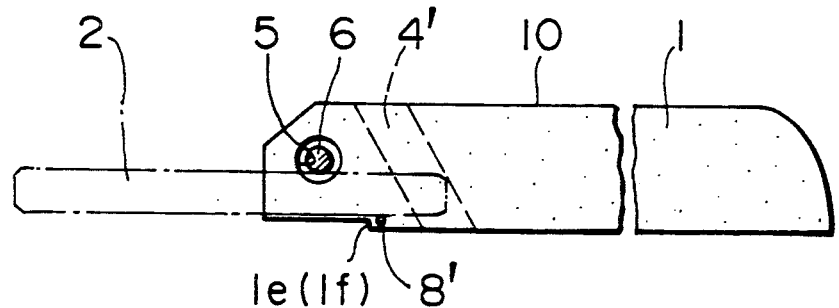
FIG. 5 is a sectional view similar to FIG. 3, illustrating a variant form of the holder shown in FIG. 3.

Referring to FIG. 5 in which a variant form of the second embodiment of the present invention is shown, the through-bore 4' is inclined in the direction reverse to that mentioned above. In this arrangement, the top corner part of the inserted end part of the microtome blade 2 bears against the innermost part of the wall surface of the through-bore 4' while the bottom corner part of the blade bears against the blade hold pin 8' embedded in the bottom side projecting parts 1e and 1f, and accordingly, it is possible to prevent the microtome blade 2 from being turned in both directions.

The holder having the arrangement as mentioned above, according to the present invention, has a less number of necessary components and a simple structure, and accordingly can be manufactured easily at a low cost. Further, the attaching of a microtome blade to the holder of this invention can be done easily and safely since the microtome blade can be stably borne against the wall surface of the inclined through-bore and the shank of the thumb screw, and the microtome blade having been attached thereto can be prevented from being turned during the use, thereby it is possible to efficiently and safely reuse the used microtome blade.

Although the preferred embodiments of the present invention have been explained, in detail, hereinabove, the present invention should not be limited to these embodiments alone, but various modifications and changes can be made thereto without departing from the scope of the invention defined in the appended claims.

What we claim is:

1. A holder for clamping a used microtome blade for reusing, comprising:

a holder body having a longitudinal axis and front and grip end portions, said front end portion having an end face, bifurcated half parts formed by cutting said front end portion and extending therethrough so as to define a slit therebetween which extends inward of said holder body from the front end of said front end portion in a plane passing through said longitudinal axis;

an inclined through-bore formed through the front end portion so as to terminate said slit, having a wall surface including an innermost part; and, means for clamping a used microtome blade inserted in said slit;

whereby said through-bore is inclined so that a corner part of the inserted microtome blade bears against the innermost part of the wall surface of said through-bore.

2. A holder as set forth in claim 1, wherein said through-bore is inclined so that a bottom corner part of the inserted microtome blade bears against the innermost part of the wall surface of said through-bore.

3. A holder as set forth in claim 1, wherein said through-bore is inclined so that a top corner part of the inserted microtome blade bears against the innermost part of the wall surface of said through-bore.

4. A holder as set forth in claim 1, wherein said clamping means includes a thumbscrew extending through a hole formed in one of said bifurcated half parts and screwed into a female thread hole formed in the other one of said bifurcated half parts.

5. A holder as set forth in claim 1, wherein said through-bore has a circular-cross sectional shape.

6. A holder as set forth in claim 1, wherein graduations are provided on the grip end portion of the holder body so that the grip end portion serves as a measure.

7. A holder as set forth in claim 1, wherein a blade hold pin is fitted between said bifurcated half parts.

8. A holder as set forth in claim 7, wherein said blade hold pin receives a top side face of the inserted microtome blade.

9. A holder as set forth in claim 7, wherein said blade hold pin receives a bottom corner part of the inserted microtome blade.

* * * * *